(12) United States Patent
Mialhe

(10) Patent No.: US 7,316,695 B2
(45) Date of Patent: Jan. 8, 2008

(54) VASCULAR OCCLUSION DEVICE, APPARATUS AND METHOD FOR USING SAME

(76) Inventor: Claude Mialhe, 292, Chemin de la Sirene, Draguignan (FR) F-83300

(*) Notice: Subject to any disclaimer, the term of this patent is extended or adjusted under 35 U.S.C. 154(b) by 768 days.

(21) Appl. No.: 10/363,402

(22) PCT Filed: Jul. 26, 2001

(86) PCT No.: PCT/FR01/02445

§ 371 (c)(1),
(2), (4) Date: Mar. 4, 2003

(87) PCT Pub. No.: WO02/19926

PCT Pub. Date: Mar. 14, 2002

(65) Prior Publication Data
US 2003/0153935 A1 Aug. 14, 2003

(30) Foreign Application Priority Data
Sep. 4, 2000 (FR) .................................. 00 11557

(51) Int. Cl.
A61B 17/08 (2006.01)
(52) U.S. Cl. .................................................... 606/158
(58) Field of Classification Search ................ 606/151, 606/153, 157, 191–198; 623/1.11, 1.12, 623/1.13, 158
See application file for complete search history.

(56) References Cited

U.S. PATENT DOCUMENTS

| 5,282,824 | A | * | 2/1994 | Gianturco | .................. 623/1.13 |
| 5,382,261 | A |   | 1/1995 | Palmaz |   |
| 6,063,113 | A | * | 5/2000 | Kavteladze et al. | ........ 623/1.15 |
| 6,676,657 | B2 | * | 1/2004 | Wood | .......................... 606/41 |

FOREIGN PATENT DOCUMENTS

| DE | 198 01 076 | 6/1999 |
| EP | 0 864 300 | 9/1998 |
| WO | 97 27893 | 8/1997 |
| WO | 99 07292 | 2/1999 |

* cited by examiner

*Primary Examiner*—Kevin T. Truong
(74) *Attorney, Agent, or Firm*—Young & Thompson

(57) ABSTRACT

The invention concerns a vascular occlusion device. The invention is characterized in that it comprises two expandable members (3, 4) enabling it to be fixed by pressure on two portions of the vessel; it further comprises an intermediate part (5) deformable in twisting to an adjustable degree depending on the relative position of the two expandable members (3, 4); thereby producing a maximum constricted region (6) defining the extent of occlusion. The invention also concerns a apparatus for setting and a method for using such a device.

16 Claims, 4 Drawing Sheets

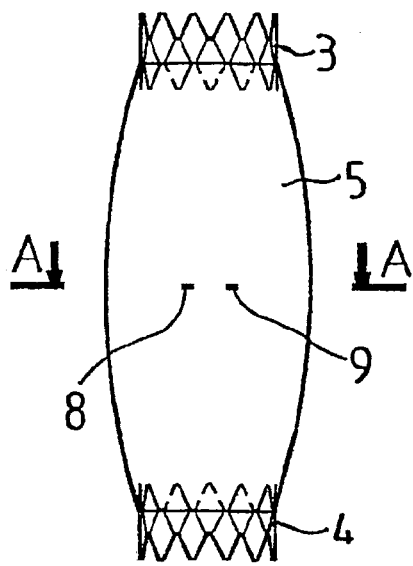
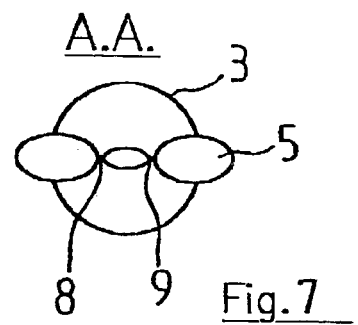
Fig. 6
Fig. 7
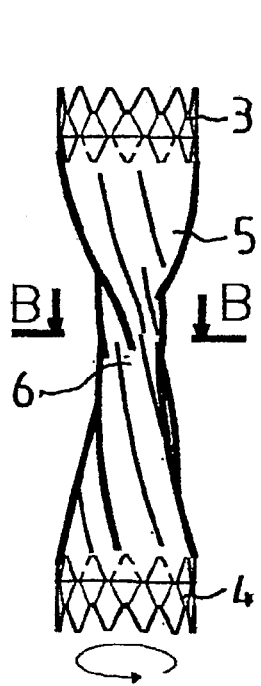
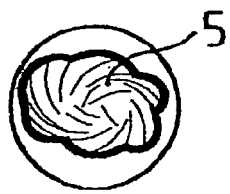
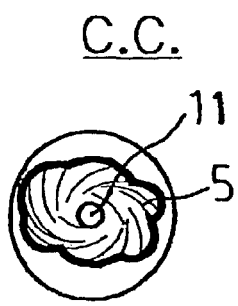
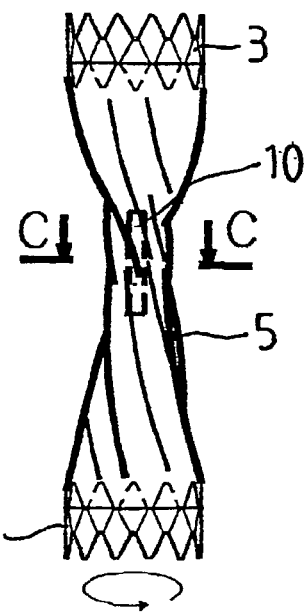
Fig. 8
Fig. 9
Fig. 10
Fig. 11

VASCULAR OCCLUSION DEVICE, APPARATUS AND METHOD FOR USING SAME

BACKGROUND OF THE INVENTION

The present invention relates principally to a device for occlusion adapted to be introduced into a vessel.

It also relates to an apparatus for emplacement of a vascular occlusion device as well as a process for use of such a device.

The invention will find its application in the field of the production and use of occlusive prostheses for any type of vessel in the human or animal body.

Vascular occlusion systems exist already but are not entirely satisfactory.

There is known from U.S. Pat. No. 5,382,261 a method and apparatus to occlude vessels.

According to this document, a permanent occlusion of a vessel is possible for a person, by use of a flexible obstruction element fixed to at least one radially expansible metallic portion, generally of tubular shape, the flexible obduration element having a substantially tubular longitudinal configuration.

According to this document, the occlusion element is a type of plug of tubular shape connected to a securement member in a vessel in the form of a stent, comprised by an expansible metallic armature.

In this prior art, the degree of occlusion is not adjustable. It will generally be total and this in a permanent manner.

It will be noted moreover that the securement of the occlusion device in the vessel takes place from a single side of the obduration element.

The forces thereon are thus concentrated when the blood pressure is applied to the interior of the occlusive system.

Other occlusive systems have been proposed, particularly that disclosed in EP0 947 168.

There is there disclosed a coated self-expansible vascular occlusion device which comprises an element in the form of a woven metallic filament comprising at least two axially spaced securement elements and fixed to the woven metallic filament.

A thin film covers at least half the device.

The woven element proposed is adapted to expand radially when it is freed within the blood vessel so as to close the blood vessel.

Upon its release, it immediately and completely produces occlusion of the vessel.

Again, this occlusion system serves to occlude the vessel totally and permanently.

Its structure is moreover complicated and has a substantial cost of production.

Moreover, the blood flow is oriented toward the periphery of the vessel, at the level of the connection of the woven element with internal walls of this vessel.

As a result, important forces arise because of the blood pressure which is applied.

To obtain effective sealing, it is thus necessary to provide a high expansive force on the woven element against the internal wall of the vessel.

There is also known from the document DE-C-19 801 076 an expansible member for implantation in a vessel. According to this document, the member comprises two zones 16, 18 adapted to be relatively fixed to the wall of the vessel to hold the member. An intermediate hollow portion is moreover present to ensure the passage of the flow of blood. This device constitutes essentially an accessory for carrying out surgical procedures adapted to short-circuit a vessel. It is not an occlusion device, and no deformation by torsion is present.

SUMMARY OF THE INVENTION

The present invention has for its object to overcome the drawbacks of the devices known until now.

It also permits providing a plurality of uses of the occlusion device in question.

Thus, a first object of the invention is to permit as desired obtaining a total or only partial occlusion.

The device in question could also be adapted according to the pathology to be treated.

A partial occlusion will be achieved, for example for the treatment of venous valvular insufficiencies.

On the other hand, a complete occlusion is also possible, for example for the treatment of certain arterial aneurisms.

It has the advantage, for this purpose, to provide occlusion by torsion of an intermediate portion between two expansible members securable to the wall of the vessel.

It is possible to modify or adjust the degree of torsion applied to the intermediate portion so as to adjust the level of occlusion achieved.

The facility of achieving occlusion and emplacing the device according to the invention also permits envisaging temporary occlusions.

Thus, the device could be removable and withdrawn at the end of treatment.

Such a possibility could be useful for example in the formation of anti-embolism devices for cerebral protection during angioplasties or dilatation of the carotids, of the coronaries or of the coronary bridges.

The occlusive device in question moreover has the advantage of being precise as to the adjustment of the degree of occlusion achieved.

This degree of occlusion can be adjusted according to the relative angular position of the two expansible members or else according to their longitudinal spacing.

The rotative movement also ensures an adjustment as to length in place of the device as well as the adjustment in position of the region of maximum constriction.

This device can moreover be used with securement means (expansible members) of known type and which have now been proven.

Thus, the expansible members could be self-expansible endoprostheses with shape memory or else they could be positioned by inflation of a balloon.

It will be seen accordingly that the implantation of such an occlusion device is rapid and requires only tools with which the practitioner is skilled.

An endoluminal intervention, final or not, can thus be carried out by reducing the time of intervention.

The device can also be applied to hemostasis of the vessels after transparietal puncture and, generally, to any type of parietal occlusion.

Other objects and advantages will be become apparent from the description which follows, which is however given only by way of indication and not for limitation of the invention.

The present invention relates to an occlusion device adapted to be introduced into a vessel, characterized by the fact that it comprises two hollow expansible members for its securement by bearing against two portions of the wall of the vessel and a hollow intermediate portion deformable in torsion to a degree adjustable according to the relative position of the two expansible members, to create a region of maximum constriction defining the degree of occlusion.

This device could be embodied in the modifications set forth hereafter:

the expansible members are pivotal about the longitudinal axis of the device to twist the intermediate portion to a degree adjustable according to their relative angular position.

it comprises means for positioning the maximum constriction region.

the positioning means comprise at least one punctual connection of two regions of the wall of the intermediate portion.

it comprises two punctual connections at a same level along the length of the intermediate portion.

it comprises a hollow tubular member disposed between the two punctual connections to define a residual opening.

the tubular member comprises, in its interior volume, a non-return valve.

the positioning means comprise folds on the surface of the intermediate portion, the folds being concurrent toward the region of maximum constriction.

the intermediate portion is tubular and has two pairs of folds oriented each according to a diagonal arc of a half of the intermediate portion seen in longitudinal cross-section, the folds of each pair being formed on opposite sides of the region of maximum constriction and being of increasing thickness in its direction.

it comprises two other pairs of folds of a shape similar to the two first ones and oriented according to the two complementary diagonal arcs.

the folds have a semi-helicoidal shape.

The invention also relates to an apparatus for emplacing the vascular occlusion device, comprising two hollow expansible members for its securement by bearing against two portions of the wall of the vessel, and an intermediate portion which is hollow and deformable in torsion to a degree adjustable according to the relative angular position of the two expansible members, adapted to be used for the emplacement of a device according to the invention, characterized by the fact that it comprises:

two cylindrical hollow sleeves, the outer one receiving the first expansible member and at least one portion of the intermediate portion, the other internal one being movable pivotally slidably in the outer sleeve, adapted to exert a pressure on the first expansible member, and receiving the second expansible member, a piston sliding in the internal sleeve and adapted to exert a pressure on the free end of the second expansible member.

It also relates to a process for the use of an implantable vascular occlusion device in the vessel of an individual, adapted to be used by the device according to the invention, characterized by the fact that there is used a vascular occlusion device comprising two hollow expansible members for its securement by bearing against two portions of the wall of the vessel and an intermediate hollow portion deformable in torsion, a first expansible member is secured, the second expansible member is pivoted relative to the first so as to give rise to torsion in the intermediate portion, the second expansible member is fixed in a pivoted position adjusted according to the desired degree of occlusion.

BRIEF DESCRIPTION OF THE DRAWINGS

The accompanying drawings are given by way of indicative and non-limiting example. They show a preferred embodiment according to the invention. They permit easy comprehension of the invention.

FIG. 6 shows a second embodiment of the vascular occlusion device also seen in cross-section on the line A-A in FIG. 7.

FIGS. 8 and 9 show respectively a longitudinal view and a cross-sectional view on the line B-B of a torsion device according to the embodiment of FIG. 6 in a configuration in which the intermediate portion is deformed by torsion.

FIGS. 10 and 11 show respectively a longitudinal view and a cross-sectional view on the line C-C of the occlusion device according to the invention in an embodiment in which a tubular member is present.

FIG. 4 shows schematically a first embodiment of the occlusion device according to the invention.

DESCRIPTION OF THE PREFERRED EMBODIMENTS

Figure 4:
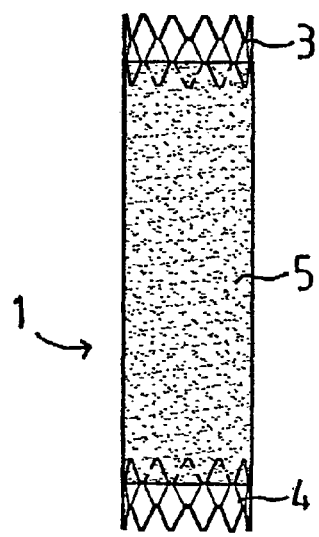
FIG. 4 shows the general structure of the occlusion device according to the invention in a first embodiment and FIG. 5 shows schematically a configuration with torsion of the intermediate portion.

This device comprises two expansible members 3, 4 seen in FIG. 4 at the two ends of the device.

The expansible members 3, 4 have the function of ensuring the securement of the device in the vessel 2 by bearing on two portions of its internal wall.

Preferably, but not limitingly, the two expansible members 3, 4 can be constituted by armatures of the self-expansible stent type with shape memory or else deformable by inflation of a balloon.

Between the two expansible hollow members 3, 4 there is an intermediate portion 5 also seen in FIG. 4.

The intermediate portion 5 is hollow and deformable by torsion.

It can for example be constituted by a suitable textile.

Preferably, the assembly of the device thus produced has a substantially hollow tubular shape.

As is indicated above, the intermediate portion 5 is deformable by torsion.

Figure 5:
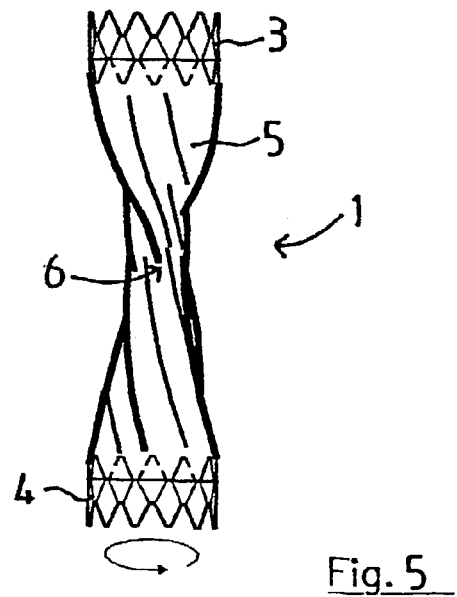

An example of this deformation is shown in FIG. 5.

As indicated schematically by the arrows, the deformation by torsion can be produced by a relative angular displacement of the expansible members 3, 4.

There can for example be a pivot at the level of the armature of the expansible member 4 relative to the expansible member 3 which will itself remain fixed.

The deformation by torsion of the intermediate portion 5 leads to the production of a region of maximum constriction 6 which, as in FIG. 5, is positioned substantially halfway along the length of the intermediate portion 5.

The region of maximum constriction 6 is, according to the degree of torsion, the site of a partial or total occlusion.

Thus, for example, beyond an angular offset of the expansible members 3, 4 greater than a predetermined limit (for example between 180 and 360°), the occlusion will be total.

This side of that value, the occlusion will be partial.

It is useful to be able to position precisely the region of maximum constriction 6.

To this end, FIGS. 6 and 7 show a second embodiment of the occlusion device 1.

In this figure, the positioning means for the region of maximum constriction 6 are seen in the form of two punctual connections 8, 9.

Preferably, the punctual connections 8, 9 are sutures produced on the intermediate portion initially constituted by a hollow tubular element.

There will preferably be formed two punctual connections 8, 9 located at the same level along the length of the intermediate portion 5 and positioned on opposite sides of the longitudinal axis 7 of symmetry of the tubular intermediate portion 5.

It will be noted in FIGS. 8 and 9 that the torsion of the intermediate portion 5 is thus precisely oriented by the punctual connections 8, 9 and that the region of maximum constriction 6 is perfectly situated.

Moreover, in a particular embodiment, the punctual connections 8, 9 permit constituting a reservation adapted to receive a tubular member 10.

This is disposed between the two punctual connections 8, 9 and defines a residual opening 11 shown in FIG. 11.

A partial occlusion, limiting the passage of blood flow to a well-defined section, can thus reliably be carried out with a partial occlusion.

Moreover, for the treatment of certain pathologies, the tubular member 10 can be the site of implantation of a non-return valve.

Thus, the occlusion device in question assures complete occlusion in one direction and partial occlusion in the other direction of blood flow.

As indicated above, it is desirable also to be able to position as precisely as possible the region of maximum constriction 6.

Supplemental to, or instead of, the punctual connections 8, 9, there could for this purpose be provided other positioning means.

Thus, the folds 12 formed at the external or internal surface of the intermediate portion 5 can ensure the positioning and promote a first orientation of the torsion.

FIGS. 12 to 16 show successively, different modifications of embodiment and of configuration of the folds 12.

Preferably, the folds are formed on the external surface of the intermediate portion 5 constituted by a hollow tubular textile element.

The folds are concurrent toward the region of maximum constriction 6, as is shown in FIGS. 12 to 16.

Figure 12:
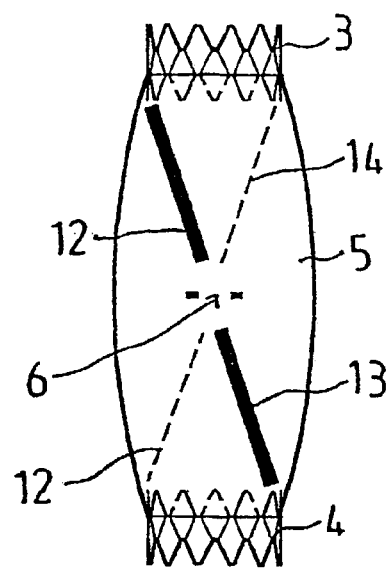
FIGS. 12 to 16 show other embodiments of the invention in which the folds are constituted on the surface of the intermediate portion.

According to FIG. 12, there are formed two pairs 13, 14 of folds 12.

One pair 13 is located on one half of the intermediate portion 5, the other pair 14 is located on the other half of the intermediate portion 5.

There is meant by "half", a portion of the intermediate portion which, seen in longitudinal cross-section, is located on one side of the cutting plane.

In this configuration, the pairs 13, 14 are oriented along two diagonal arcs of the intermediate portion 5 in the configuration shown in FIG. 12.

Each diagonal arc has two folds 12 located on opposite sides of the zone of maximum constriction 6 to be formed.

Figure 13:
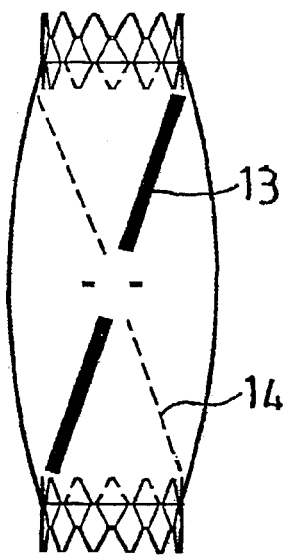

FIG. 13 shows that the pairs 13, 14 of folds can be formed located along two other diagonal arcs.

Figure 14:
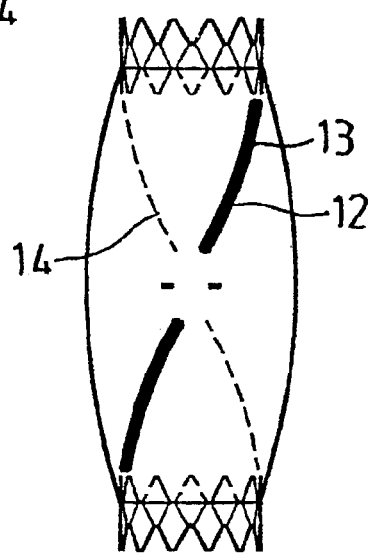

In this case of FIG. 14, the folds 12 have a semi-helicoidal shape.

Figure 15:
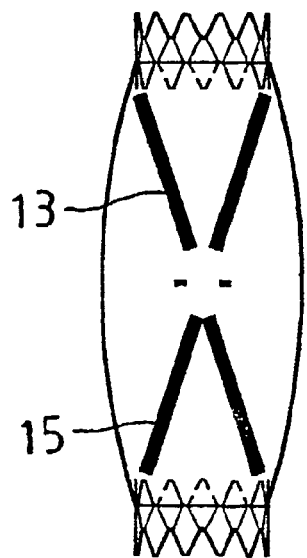

In FIG. 15, there is shown an embodiment in which, in addition to the pairs 13 or 14 of folds 12, there are provided supplemental pairs 15 permitting, on each half of the intermediate portion 5, providing two pairs of folds.

Figure 16:
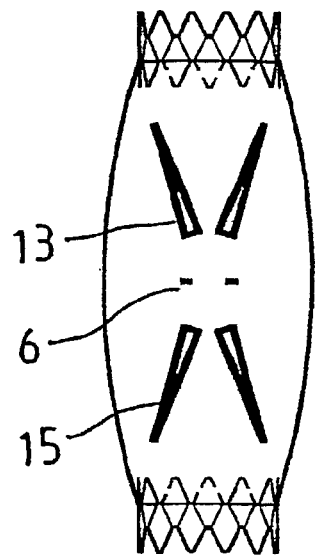

Finally, FIG. 16 shows another modified embodiment of the folds 12 in the sense that each fold 12 has a thickness increasing in the direction of the zone of maximum constriction 6.

A fold of substantially triangular configuration is thus provided in this embodiment.

It will be easily understood that the formation of the folds 12 facilitates the deformation in torsion of the intermediate portion 5 and fixes in a precise manner the location of the region of maximum constriction 6.

The occlusion device 1 thus prepared can be emplaced by means of the apparatus described hereafter, which forms an integral portion of the present invention.

Figure 1:
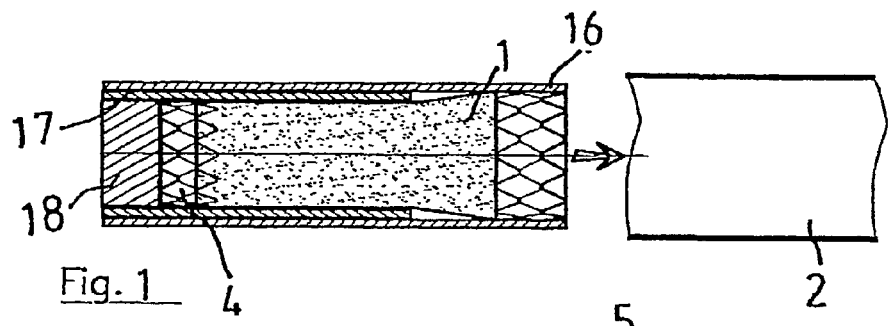
FIGS. 1 and 2 show the steps in use of the occlusion device according to the invention, as well as the phases of use of the emplacement apparatus.

Referring to FIG. 1, it will be seen that the occlusion device 1 is integrated in an apparatus comprising two sleeves, an outer sleeve 16 and an inner sleeve 17.

The occlusion device 1 is located such that one of the expansible members 3 is maintained in compressed position by one of the sleeves, for example the external sleeve 16.

The other expansible member 4 is maintained in compressed position by the inner sleeve 17.

The intermediate portion 5 extends between the two expansible members 3, 4 and is located partially in the internal sleeve 17 and partially in the external sleeve 16.

The sleeves 16, 17 are of course adapted in length and in diameter to the dimensions of the occlusion device 1.

Moreover, their respective diameters are selected so as to coact in the formation of a connection with a sliding pivot.

At the rear of the expansible armature 4 is provided a piston 18 also visible in FIG. 1.

This piston is in the internal sleeve 17 so as to bear against the distal end of the armature of the member 4.

The apparatus thus provided can be used in the following manner.

The apparatus is introduced into a portion of the vessel 2 at the region where occlusion is desired.

Figure 2:
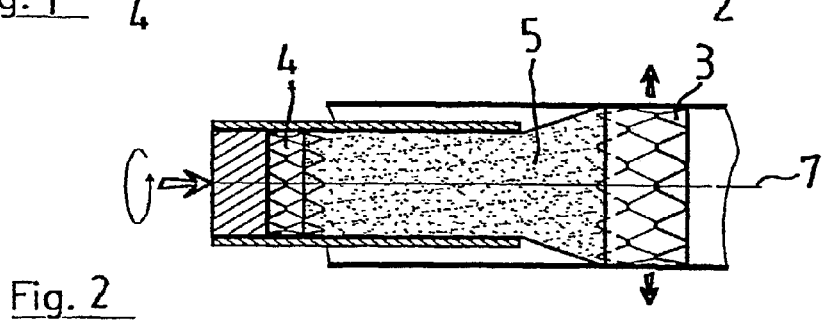

Referring to FIG. 2, it will be seen that by retracting the external sleeve 16 relative to the internal sleeve 17, it is possible to free the expansible member 3.

If this member 3 is of the self-expanding type, its securement on the internal wall of the vessel will be produced at the outset.

It is also possible to carry out this securement by inflation of a balloon within the expansible member.

At this emplacement step, the second expansible member 4 is free in rotation and in axial displacement relative to the first expansible member 3.

The intermediate portion 5 undergoes deformations particularly in torsion as a function of the movement imposed on the expansible member 4.

This movement is produced by relative movement of the external sleeve 17 and the piston 18. The piston 18 can be of the type commonly called a "pusher" in the field in question.

Thus, the rotation by the practitioner of the sleeve 17 gives rise to the deformation in torsion of the intermediate portion 5 and the corresponding approach to each other of the two expansible members 3, 4.

Once the desired relative position of the expansible members 3, 4 is obtained, the second expansible member 4 is freed.

This freeing takes place by withdrawing the internal sleeve 17 whilst maintaining the piston 8 in bearing against the expansible member 4.

Figure 3:
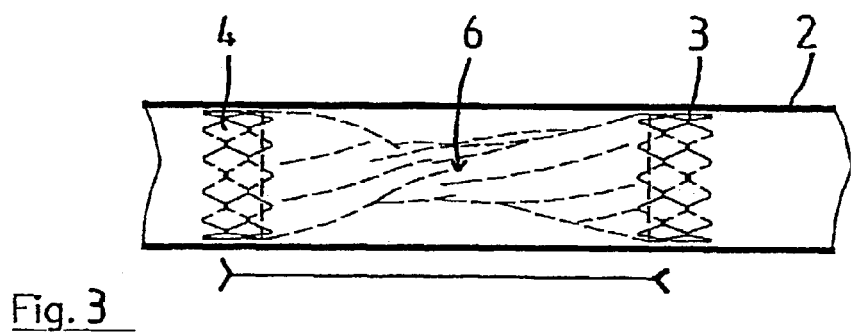
FIG. 3 shows an example of embodiment of the occlusion device once implanted in a vessel.

After retraction of the assembly of the apparatus, a final implantation position is reached, as shown in FIG. 3.

In the course of the operation, it will be seen that the adjustment of the degree of occlusion is perfectly adjusted during movement imparted to the sleeve 17 particularly by rotation imposed on it.

Of course, the apparatus could comprise different markings particularly for angular longitudinal movement of the sleeve 17 relative to the piston 18, to adjust the torsion to be produced on the intermediate portion 5.

The process of use which also forms a portion of the invention can be carried out by the apparatus and the occlusion device 1 which have been previously described.

These steps of production are also to be seen particularly in FIGS. 1 to 3.

After securement of the expansible member 3, on the internal walls of the vessel 2, the second expansible member 4 is pivoted relative to the first so as to give rise to a torsion in the intermediate portion 5.

It is then possible to fix the second expansible member 4 in the adjusted pivoted position according to the desired degree of occlusion.

It will be noted that a central guide can be incorporated in the emplacement apparatus in the form of a filament or catheter at the center of the device to be implanted, to take part in the movement of the device and possible accessories for emplacement in the vessel.

The central guide is, in a modified embodiment, associated with a balloon which can be releasable so as to remain at the level of one of the ends of the implanted device.

Figure 17:
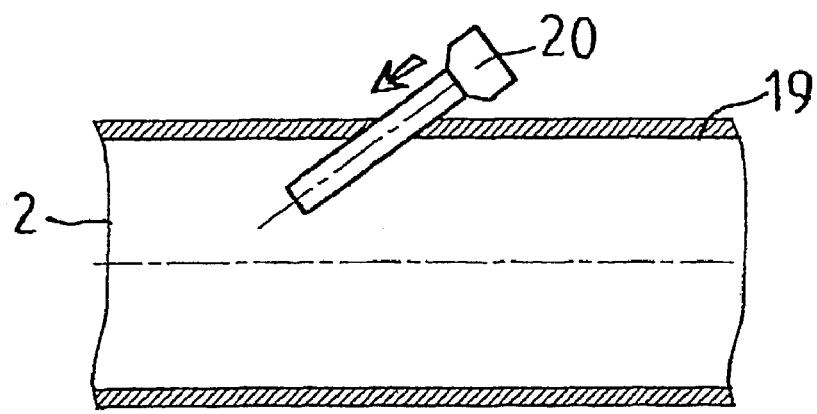
FIGS. 17, 18 and 19 show an application of the invention to a parietal occlusion.
Figure 18:
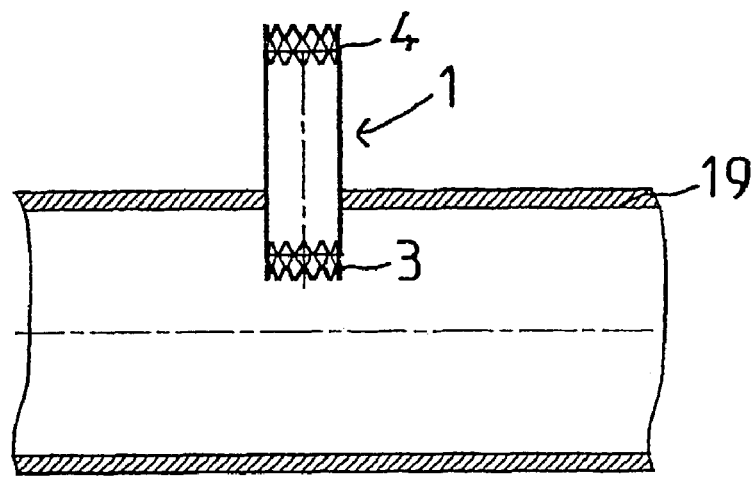
Figure 19:
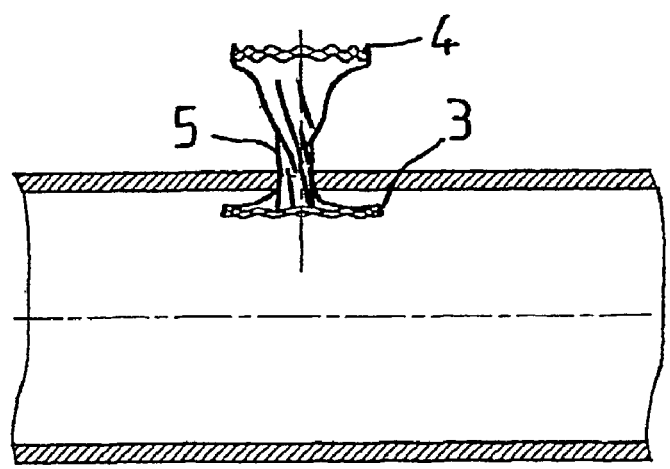

FIGS. 17 to 19 show an application of the occlusion device 1 to a parietal occlusion.

It can happen that the practitioner must form a passage in the wall 19 of the vessel 2, particularly during punctures.

The invention offers a possibility of closing the passage.

FIG. 17 shows the trans-parietal introduction of a surgical instrument. A passage in the wall 19 is thus formed.

In FIG. 18, a device 1 is introduced through the passage in the wall 19. One of its ends 3 constituted by expansible members is thus inserted in the internal volume of the vessel 2. The other member 4 is maintained outside the vessel 2.

By expansion, the member 3 is applied against the internal wall of the vessel 2 whilst the member 4, after torsion, is applied to the external wall.

FIG. 19 shows the deformation applied to the device for this use.

The intermediate portion 5 plugs the passage formed during the surgical intervention.

REFERENCES

1. Occlusion device
2. Vessel
3, 4. Expansible members
5. Intermediate portion
6. Zone of maximum constriction
7. Longitudinal axis
8, 9. Punctual connections
10. Tubular member
11. Residual opening
12. Folds
13, 14. Pairs of folds
15. Pair of supplemental folds
16. External sleeve
17. Internal sleeve
18. Piston
19. Wall
20. Instrument

The invention claimed is:

1. Occlusion device (1) adapted to be introduced into a vessel (2), comprising two hollow expansible members (3, 4) for securement of the device in bearing against two portions of the wall of the vessel (2), and an intermediate hollow portion (5), wherein the intermediate hollow portion (5) extends along a longitudinal axis (7) of the device between the two hollow expansible members (3, 4), each end of the intermediate hollow portion (5) being joined to a respective one of the two hollow expansible members (3, 4), the two expansible members being independently rotatable, and wherein the intermediate hollow portion (5) is deformed in torsion by relative rotational motion of the two expansible members to a degree adjustable according to the relative angular position of the two expansible members (3, 4) to create a zone of maximum constriction (6) defining the degree of occlusion.

2. Occlusion device (1) according to claim 1, wherein the expansible members (3, 4) pivot about the longitudinal axis (7) of the device (1) to twist the intermediate portion (5) to a degree adjustable according to their relative angular position.

3. The occlusion device of claim 2, wherein the hollow expansible members have a non-zero angular offset relative to a reference position in which the intermediate hollow portion is not deformed by torsion.

4. The occlusion device of claim 3, wherein the non-zero angular offset is less than 180°.

5. The occlusion device of claim 3, wherein the non-zero angular offset is greater than 180°.

6. The occlusion device of claim 3, wherein the non-zero angular offset is between 180° and 360°.

7. The occlusion device of claim 1, wherein an interior of the intermediate hollow portion constricts to form the zone of maximum constriction.

8. The occlusion device of claim 1, wherein the intermediate hollow portion comprises a textile.

9. The occlusion device of claim 1, wherein the intermediate hollow portion is a tube.

10. Apparatus for emplacing a vascular occlusion device comprising first and second hollow expansible members (3, 4) that are independently rotatable against two portions of the wall of the vessel (2) and an intermediate hollow portion (5) deformable in torsion by relative rotational motion of the first and second expansible members to a degree adjustable according to the relative angular position of the two expansible members (3, 4), the apparatus comprising two hollow cylindrical sleeves, one of the two sleeves being an external sleeve (16) receiving the first expansible member (3) and at least one portion of the intermediate portion (5), the other of the two sleeves being an internal hollow cylindrical sleeve (17) that is movable in the external sleeve (16), and being adapted to exert a pressure on the first expansible member (3), and receiving the second expansible member (4), a piston (18) sliding in the internal sleeve (17) and adapted to exert a pressure on the free end of the second expansible member (4).

11. Process for using a vascular occlusion device implantable in a vessel (2) of an individual, comprising the steps of:
providing a vascular occlusion device comprising first and second hollow expansible members (3, 4) that are independently rotatable for securement of the device by bearing against two portions of the wall of the vessel (2), and an intermediate hollow portion (5) deformable by torsion caused by relative rotational motion of the first and second expansible members,
fixing the first expansible member,
rotating the second expansible member (4) relative to the first hollow expansible member so as to cause torsion of the intermediate portion (5),
fixing the second expansible member (4) in a rotated position adjusted according to the desired degree of occlusion.

12. The process of claim 11, wherein the pivoting step pivots the second hollow extensible member relative to the first hollow extensible member to create a non-zero angular offset between the first and second hollow extensible members.

13. The process of claim 12, wherein the non-zero angular offset is less than 180°.

14. The process of claim 12, wherein the non-zero angular offset is greater than 180°.

15. The process of claim 12, wherein the non-zero angular offset is between 180° and 360°.

16. A combination of an occlusion device adapted to be introduced into a vessel and an apparatus for emplacing the occlusion device in the vessel;
said occlusion device comprising first and second hollow expansible members and an intermediate hollow portion, the intermediate hollow portion extending along a longitudinal axis of the occlusion device between the first and second hollow expansible members, each end of the intermediate hollow portion being joined to a respective one of the first and second hollow expansible members, the first and second expansible members being independently rotatable, the intermediate hollow portion being deformed in torsion by relative rotational motion of the first and second expansible members to a degree adjustable according to the relative angular position of the first and second expansible members to create a zone of maximum constriction defining the degree of occlusion; and
said apparatus comprising two hollow cylindrical sleeves, one of the two sleeves being an external sleeve receiving the first expansible member and at least one portion of the intermediate portion, the other of the two sleeves being an internal hollow cylindrical sleeve that is movable in the external sleeve, that exerts pressure on the first expansible member and that receives the second expansible member, the internal sleeve being rotatable to adjust the relative angular position of the first and second expansible members, and a piston sliding in the internal sleeve and exerting pressure on a free end of the second expansible member.

* * * * *